(12) United States Patent
Taniguchi

(10) Patent No.: US 6,638,406 B2
(45) Date of Patent: Oct. 28, 2003

(54) HYDROCARBON SENSOR AND METHOD FOR PRODUCING THE SAME

(75) Inventor: Noboru Taniguchi, Osaka (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 41 days.

(21) Appl. No.: 09/976,196

(22) Filed: Oct. 11, 2001

(65) Prior Publication Data

US 2002/0070109 A1 Jun. 13, 2002

(30) Foreign Application Priority Data

Oct. 16, 2000 (JP) ........................................ 2000-315749

(51) Int. Cl.⁷ ............................................. G01N 27/407
(52) U.S. Cl. .................. 204/424; 204/421; 204/426; 204/292; 204/293; 205/787; 427/123; 427/125; 427/126.4
(58) Field of Search ................... 204/421–429

(56) References Cited

U.S. PATENT DOCUMENTS 5,935,398 A * 8/1999 Taniguchi et al.
6,238,535 B1  5/2001 Taniguchi et al.
2001/0010290 A1  8/2001 Taniguchi

FOREIGN PATENT DOCUMENTS

| EP | 949 505 | 10/1999 |
|---|---|---|
| EP | 1 041 380 A2 | 10/2000 |
| JP | 57-28248 | 2/1982 |
| JP | 10-48175 | 2/1998 |
| JP | 10-300718 | 11/1998 |
| JP | 11-337518 | 12/1999 |
| JP | 2000-146902 | 5/2000 |

* cited by examiner

Primary Examiner—T. Tung
(74) Attorney, Agent, or Firm—Merchant & Gould P.C.

(57) ABSTRACT

A hydrocarbon sensor of the present invention includes a substrate made of a solid electrolyte that conducts protons, and a pair of electrodes formed on the substrate, and at least one electrode of the pair of electrodes contains Au and Al. Assuming that a content of an Al simple substance in one of the pair of electrodes is "a" mol %, and a content of aluminum oxide therein is "b" mol %, "a" and "b" satisfy a relationship: $a+2b \leq 7$.

2 Claims, 3 Drawing Sheets

HYDROCARBON SENSOR AND METHOD FOR PRODUCING THE SAME

BACKGROUND OF THE INVENTION

1. Field of the Invention

The present invention relates to a hydrocarbon sensor and a method for producing the same.

2. Description of the Related Art

Some known hydrocarbon sensors are capable of detecting hydrocarbon in a living environment and hydrocarbon in exhaust gas from an automobile engine, a heater, and catalytic combustion equipment, and can be used for combustion control (leanburn) of a combustion engine or combustion equipment.

As a sensor for measuring or detecting hydrocarbon, a hydrocarbon sensor is known, which includes a thin substrate made of a proton conductor that is a solid electrolyte and two electrode layers made of platinum disposed on both sides of the substrate so as to be opposed to each other. In such a hydrocarbon sensor, hydrocarbon in an atmosphere to be measured is dissociated at an anode to generate protons. The protons move in the substrate made of an electrolyte. The sensor detects the protons as a voltage or a current flowing between the electrodes.

In order to use the above-mentioned hydrocarbon sensor for a combustion engine and combustion equipment, it is required to provide a proton conductor made of an oxide that can be used at room temperature or higher. In recent years, as a proton conductor made of an oxide, $CaZr_{0.9}In_{0.1}O_{3-\alpha}$ (where $\alpha$ indicates a stoichiometric deficiency of oxygen, which applies to the rest of the specification) that is a calcium zirconium type oxide, has been developed, and an attempt has been made to apply such a proton conductor to a hydrocarbon sensor.

The above-mentioned calcium zirconium type oxide has a small proton conductivity (e.g., about $5\times10^{-4}$ S/cm at 600° C.). Therefore, the inventors of the present invention have proposed a hydrocarbon sensor of a limiting current type (constant-potential electrolysis type) using a barium cerium type oxide that exhibits a high proton conductivity (see JP 10(1998)-300718 A). The sensor responds to hydrocarbon satisfactorily, and substantially linearly can detect hydrocarbon on the order of several ppm to several % in the absence of oxygen.

However, in the case of hydrocarbon of low concentration (e.g., 10 ppm or less), the output of the sensor using a barium cerium type oxide is influenced by the concentration of oxygen. This is because a barium cerium type oxide has a property of conducting oxide ions, and the output of the sensor fluctuates due to the oxygen passed through a cathode. Therefore, the inventors of the present invention have developed a sensor that inhibits the entry of oxygen by using a cathode mainly containing metallic aluminum (see JP 11(1999)-337518 A). The effect of a cathode containing metallic aluminum is so great that the output of the sensor using such a cathode does not increase even when a small amount of oxygen is mixed in the gas to be measured.

The above-mentioned sensor has a problem in that a hydrocarbon detection ability is decreased in the case of oxygen of high concentration. In the case where exhaust gas from an automobile engine is purified with a catalyst, when the performance of the catalyst is degraded, a hydrocarbon (HC) component of high concentration and oxygen of high concentration may be mixed in the exhaust gas. Thus, a conventional sensor does not have characteristics sufficient for detecting the degradation of a catalyst for purifying exhaust gas. Furthermore, in the case of measuring hydrocarbon in exhaust gas, there is a demand for a sensor enduring a heat cycle due to remarkable changes in temperature. In the case of a conventional sensor using an Al-containing electrode, Al forms a nonconductor during a heat cycle to degrade characteristics.

SUMMARY OF THE INVENTION

Therefore, with the foregoing in mind, it is a first object of the present invention to provide a hydrocarbon sensor that is unlikely to be influenced by oxygen, in which characteristics are unlikely to be degraded by heat.

It is a second object of the present invention to provide a method for producing a hydrocarbon sensor that is unlikely to be influenced by oxygen.

In a conventional hydrocarbon sensor, Pt or Au is used alone as a conductive adhesive between an electrode and an output lead. However, in such a conventional hydrocarbon sensor, peeling of the electrode and disconnection of the lead are likely to occur. In order to solve this problem, it is a third object of the present invention to provide a highly reliable hydrocarbon sensor.

In order to achieve the above-mentioned object, a first hydrocarbon sensor of the present invention includes a substrate made of a solid electrolyte that conducts protons, and a pair of electrodes formed on the substrate, wherein at least one electrode of the pair electrodes contains Au and Al, and assuming that a content of an Al simple substance (Al metal) in the at least one electrode is "a" mol %, and a content of aluminum oxide ($Al_2O_3$) in the at least one electrode is "b" mol %, "a" and "b" satisfy a relationship: $a+2b \leq 7$. Because of this configuration, the first hydrocarbon sensor is unlikely to be influenced by oxygen, and its characteristics are unlikely to degrade due to heat.

In the first hydrocarbon sensor, the at least one electrode may contain at least one metal selected from the group consisting of an $AuAl_2$ alloy and an Au simple substance (Au metal) in a ratio of at least 50 mol %. More specifically, the at least one electrode may contain both an $AuAl_2$ alloy and an Au simple substance in a total molar ratio of at least 50 mol %. The metal with these compositions has a high melting point, which allows an electrode with high heat resistance to be obtained.

In the first hydrocarbon sensor, the at least one electrode may contain $AuAl_2$ and an Au simple substance in a molar ratio of $AuAl_2:Au=X:1-X$, where $0.6 \leq X \leq 1$. According to this configuration, a hydrocarbon sensor provided with an electrode having a particularly high oxygen blocking ability can be obtained.

Furthermore, a second hydrocarbon sensor of the present invention includes a substrate made of a solid electrolyte that conducts protons, a pair of electrodes formed on the substrate, and leads connected to the electrodes, wherein at least one electrode of the pair of electrodes contains Au and Al, and the at least one electrode and the lead are connected to each other via a conductive adhesive containing Pt and Au or a conductive adhesive containing Al and Au. In the second hydrocarbon sensor, peeling of the electrode and disconnection of the lead are unlikely to occur, and high reliability is ensured.

In the second hydrocarbon sensor, the at least one electrode and the lead may be connected to each other via a conductive adhesive containing Al and Au, and a component of the at least one electrode may be the same as a component of metal contained in the conductive adhesive. More specifically, a metal element contained in the at least one electrode may be the same as that contained in a conductive adhesive. According to this configuration, the electrode is integrated with the conductive adhesive, whereby a higher adhesion strength can be obtained.

Furthermore, a first method for producing a hydrocarbon sensor including a substrate made of a solid electrolyte that conducts protons, and an electrode formed on the substrate, includes coating the substrate with a paste containing Au particles and Al particles, followed by baking, thereby forming the electrode containing Au and Al. According to the first production method, a hydrocarbon sensor easily can be produced that is unlikely to be influenced by oxygen.

In the first production method, a content of an Al simple substance in the electrode immediately after baking may be 7 mol % or less. According to this configuration, a hydrocarbon sensor can be produced in which characteristics are unlikely to degrade due to heat.

In the first production method, the baking may be conducted in an oxygen-free atmosphere. According to this configuration, a hydrocarbon sensor with a particularly high oxygen blocking ability can be produced.

In the first production method, the oxygen-free atmosphere may be composed of at least one gas selected from the group consisting of nitrogen gas, argon gas, helium gas, and hydrogen gas.

Furthermore, a second method for producing a hydrocarbon sensor including a substrate made of a solid electrolyte that conducts protons, an electrode formed on the substrate, and a lead connected to the electrode, includes connecting the electrode to the lead via a conductive adhesive, followed by baking in an oxygen-free atmosphere, wherein the electrode contains Au and Al. According to the second production method, a hydrocarbon sensor easily can be produced, which is unlikely to be influenced by oxygen, and in which characteristics are unlikely to degrade due to heat and an adhesion strength between the lead and the electrode is high.

In the second production method, the conductive adhesive may contain Pt and Au or contain Al and Au. According to this configuration, a hydrocarbon sensor with a higher adhesion strength between the lead and the electrode can be produced.

In the second production method, the oxygen-free atmosphere in the lead connection process may be composed of at least one gas selected from the group consisting of nitrogen gas, argon gas, helium gas, and hydrogen gas.

The hydrocarbon sensor according to the present invention can be used for detecting hydrocarbon and measuring the concentration thereof in a temperature range of 300° C. to a high temperature (e.g., 800° C.). More specifically, the hydrocarbon sensor is capable of detecting hydrocarbon in a living environment, and hydrocarbon in exhaust gas from an automobile engine, a heater, and catalytic combustion equipment, and can be used for combustion control (leanburn) of a combustion engine and combustion equipment.

These and other advantages of the present invention will become apparent to those skilled in the art upon reading and understanding the following detailed description with reference to the accompanying figures.

DESCRIPTION OF THE PREFERRED EMBODIMENTS

Hereinafter, the present invention will be described by way of illustrative embodiments with reference to the drawings.

Embodiment 1

Figure 1A:
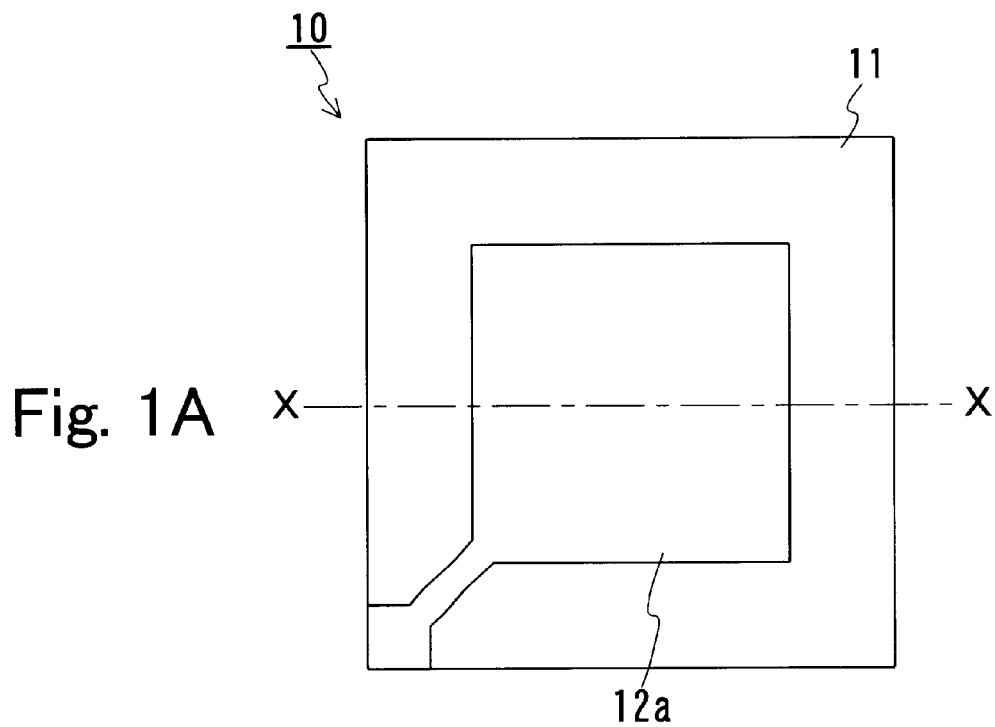
FIG. 1A is a plan view showing an example of a hydrocarbon sensor of the present invention.

In Embodiment 1, an example of a hydrocarbon sensor of the present invention will be described. FIG. 1A is a plan view of a hydrocarbon sensor 10 of Embodiment 1, and FIG. 1B is a cross-sectional view taken along line X—X in FIG. 1A.

Figure 1B:
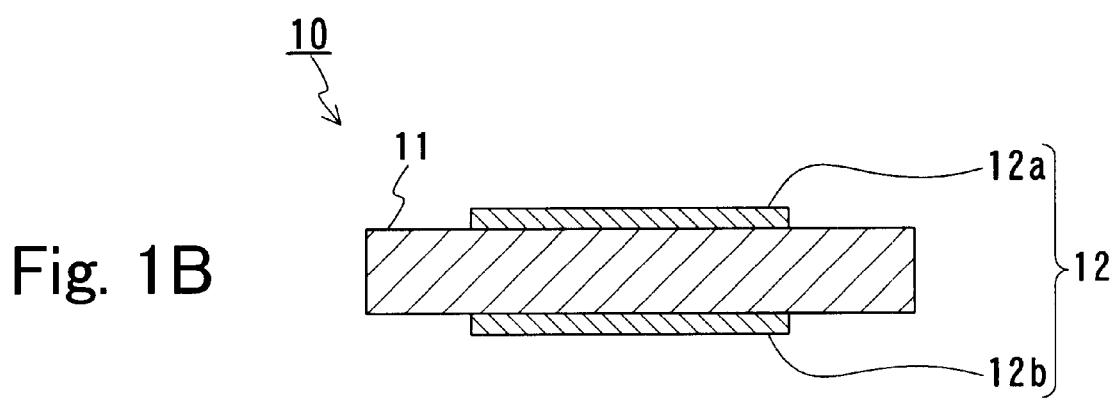
FIG. 1B is a cross-sectional view thereof.

Referring to FIGS. 1A and 1B, the hydrocarbon sensor 10 includes a substrate 11 made of a solid electrolyte that conducts protons, and a pair of electrodes 12 formed on the substrate 11. The hydrocarbon sensor 10 may be provided with leads connected to the electrodes 12, if required. In this case, it is preferable that a conductive adhesive and a lead as described in Embodiment 2 are used.

The substrate 11 is made of a solid electrolyte that conducts at least protons. For example, the substrate 11 can be made of a barium cerium type oxide such as $BaCe_{0.8}Gd_{0.2}O_{3-\alpha}$ and $BaCe_{0.8}Y_{0.2}O_{3-\alpha}$, a barium zirconium type oxide such as $BaZr_{0.8}Y_{0.2}O_{3-\alpha}$, or a barium zirconium cerium type oxide such as $BaZr_{0.6}Ce_{0.2}Gd_{0.2}O_{3-\alpha}$ and $BaZr_{0.4}Ce_{0.4}In_{0.2}O_{3-\alpha}$. Herein, $\alpha$ indicates a stoichiometric deficiency of oxygen. $\alpha$ is a value that allows a positive charge to be substantially equal to a negative charge in a solid electrolyte. For example, in the case of $BaCe_{0.8}Gd_{0.2}O_{3-\alpha}$, Ba is a divalent positive ion, Ce is a tetravalent positive ion, Gd is a trivalent positive ion, and O is a divalent negative ion, so that $\alpha=3-(2+0.8 * 4+0.2 * 3)/2 \approx 0.1$.

A pair of electrodes 12 include a cathode 12a and an anode 12b. At least one electrode (which hereinafter may be referred to as an "electrode A") selected from the cathode 12a and the anode 12b contains Au and Al. In particular, it is preferable that the cathode 12a contains Au and Al (i.e., the cathode 12a preferably is an electrode A).

Assuming that a content of an Al simple substance (i.e., Al metal) in the electrode A is "a" mol %, and a content of aluminum oxide in the electrode A is "b" mol %, the electrode A satisfies a relationship: $a+2b \leq 7$, preferably $a+2b \leq 5$. It is preferable that the value of $(a+2b)$ is as small as possible. The electrode A satisfying the relationship: $a+2b \leq 7$ can be formed, for example, by mixing TR1206 (Au paste produced by Tanaka Kikinzoku Kogyo K. K.) and 9203C (Al paste produced by Noritake Co., Ltd.) in a weight ratio of 57:43 or 54:46, followed by baking.

It also is preferable that the electrode A contains at least one metal selected from an $AuAl_2$ alloy and an Au simple substance in an amount of 50 mol % or more, preferably 75 mol % or more. It is preferable that the contents of the $AuAl_2$ alloy and the Au simple substance are as high as possible. In this case, the electrode A preferably contains $AuAl_2$ and an Au simple substance in a molar ratio of $AuAl_2:Au=X:1-X$ (where, $0.6 \leq X \leq 1$).

In the case where one of the cathode 12a and the anode 12b is not the electrode A containing Au and Al, an electrode made of Pt or an electrode made of Au can be used as such an electrode.

The electrodes 12 can be formed, for example, by coating and baking of a metal paste, solid-phase film formation, vapor deposition such as sputtering and CVD, or liquid-phase film formation such as baking.

The hydrocarbon sensor 10 of Embodiment 1 includes the electrode A containing Au and Al, so that the hydrocarbon sensor 10 has a great ability to block oxygen at electrodes. Because of this, the hydrocarbon sensor 10 is unlikely to be influenced by oxygen. Furthermore, since the amount of an Al simple substance in the electrode A is small, the characteristics of the hydrocarbon sensor 10 are unlikely to be degraded by heat.

Embodiment 2

Figure 2A:
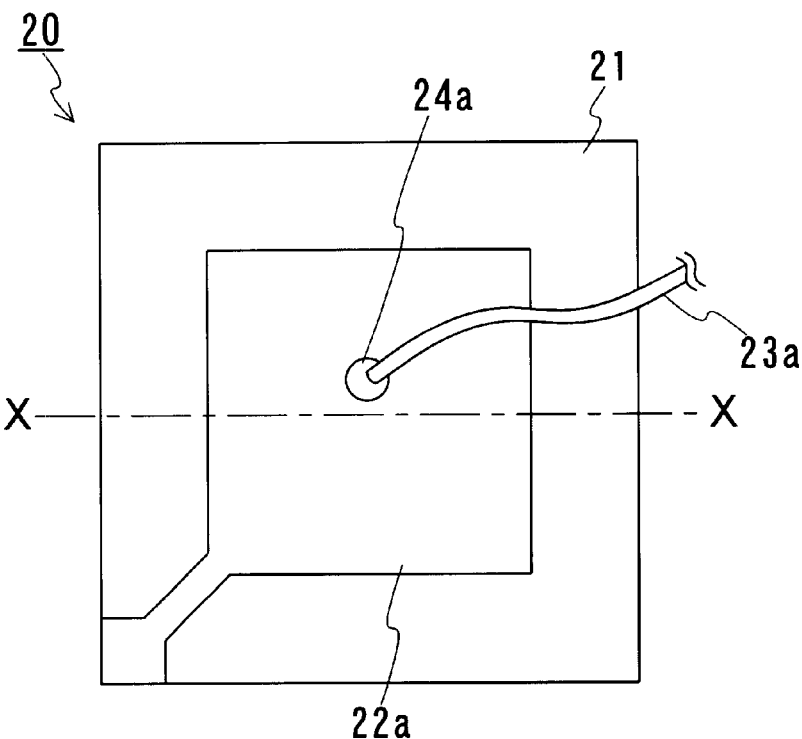
FIG. 2A is a plan view showing another example of a hydrocarbon sensor of the present invention.

In Embodiment 2, another example of a hydrocarbon sensor of the present invention will be described. FIG. 2A is a plan view of a hydrocarbon sensor 20 of Embodiment 2, and FIG. 2B is a cross-sectional view taken along line Y—Y in FIG. 2A.

Figure 2B:
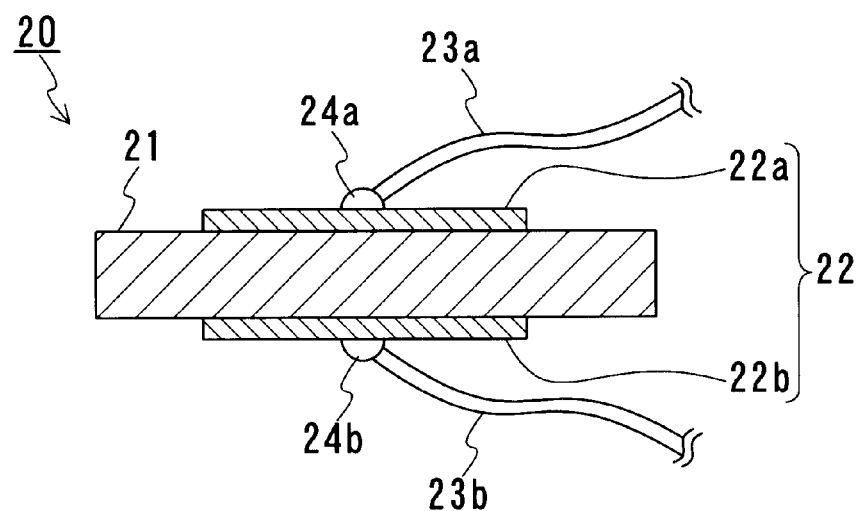
FIG. 2B is a cross-sectional view thereof.

Referring to FIGS. 2A and 2B, the hydrocarbon sensor 20 of Embodiment 2 includes a substrate 21 made of a solid electrolyte that conducts protons, a pair of electrodes 22 (including a cathode 22a and an anode 22b) formed on the substrate 21, and leads 23a and 23b respectively connected to the cathode 22a and the anode 22b.

As the substrate 21, the one similar to the substrate 11 in Embodiment 1 can be used. At least one electrode (which hereinafter may be referred to as an "electrode B") selected from the cathode 22a and the anode 22b contains Au and Al. More specifically, the same electrode as the electrode A described in Embodiment 1 can be used. In the case where one of the cathode 22a and the anode 22b does not contain Au and Al, for example, an electrode made of Pt or an electrode made of Au can be used as the electrode.

As the leads 23a and 23b, for example, those made of metal such as Pt, Au, and Ag can be used.

The cathode 22a and the anode 22b are connected to the leads 23a and 23b via conductive adhesives 24a and 24b, respectively.

As the conductive adhesives 24a and 24b, a metal paste can be used. Herein, a metal paste is obtained by adding a binder, a resin, a solvent, and the like to metal particles, if required (this also applies to the metal paste described below). Examples of the resin include poly(vinyl alcohol) (PVA) and poly(vinyl chloride) (PVC). Examples of the solvent include terpineol and butyl acetate.

Among the conductive adhesives 24a and 24b, a conductive adhesive (which hereinafter may be referred to as a "conductive adhesive B") connecting the electrode B to the lead contains Pt and Au, or Al and Au. Specifically, a conductive adhesive containing Pt and Au as its main components (in an amount of 50 mol % in total) or a conductive adhesive containing Al and Au as its main components (in an amount of 50 mol % or more in total) can be used. More specifically, a metal paste containing Pt particles and Au particles or a metal paste containing Al particles and Au particles can be used. Herein, in the case where a conductive adhesive containing Al and Au is used as the conductive adhesive B, it is preferable that the components and composition of the electrode B are the same as those of metal contained in the conductive adhesive B.

In the hydrocarbon sensor 20 of Embodiment 2, it is preferable that the conductive adhesive B connecting the electrode B containing Au and Al to the lead contains Pt and Au or Al and Au. Thus, in Embodiment 2, a highly reliable hydrocarbon sensor with a high adhesion strength between the electrode and the lead can be obtained, as described later in the examples.

Embodiment 3

In Embodiment 3, an example of a method for producing a hydrocarbon sensor of the present invention will be described. Embodiment 3 is directed to a method for producing a hydrocarbon sensor including a substrate made of a solid electrolyte that conducts protons, electrodes formed on the substrate, and leads connected to the electrodes. FIG. 3 shows processes of a production method of Embodiment 3.

Figure 3A:
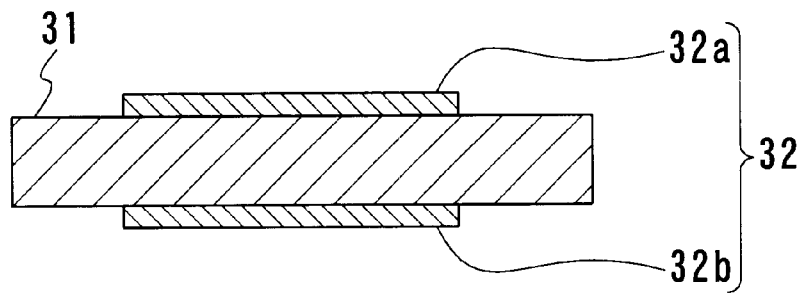
FIGS. 3A to 3C are cross-sectional views illustrating exemplary processes of a method for producing a hydrocarbon sensor of the present invention.

First, as shown in FIG. 3A, both surfaces of a substrate 31 are coated with a paste, whereby two layers 32 (layers 32a and 32b) are formed. As the substrate 31, the one similar to the substrate 11 as described in Embodiment 1 can be used.

At least one selected from the layers 32a and 32b is formed of a paste (which may be referred to as a "paste C") containing Au particles and Al particles. In the case where one of the layers 32a and 32b is not formed of a paste containing Au particles and Al particles, such a layer may be formed of a paste containing only Au particles or only Pt particles. These layers can be formed, for example, by screen-printing. The thickness of these layers is about 10 μm.

The paste C can be formed, for example, by mixing an Au paste containing Au particles and an Al paste containing Al particles.

Figure 3B:
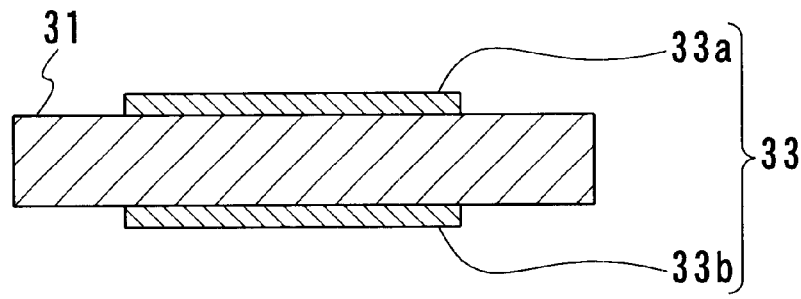

Thereafter, the substrate 31 with the layers 32a and 32b formed thereon is baked, whereby a pair of electrodes 33 (cathode 33a and anode 33b) are formed on the substrate 31, as shown in FIG. 3B. It is preferable that the baking process is conducted in an oxygen-free atmosphere. Examples of the oxygen-free atmosphere include an atmosphere composed of at least one gas selected from nitrogen gas, argon gas, helium gas, and hydrogen gas. At least one electrode selected from the cathode 33a and the anode 33b is to contain Au and Al.

Figure 3C:
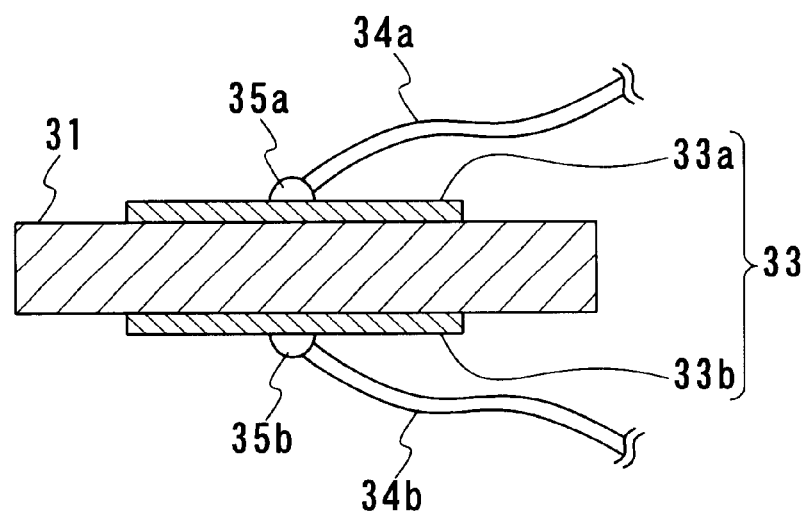

Thus, a hydrocarbon sensor can be produced. After the process in FIG. 3B, the electrodes 33a and 33b may be connected to leads 34a and 34b via conductive adhesives 35a and 35b, respectively, as shown in FIG. 3C. This lead connection process preferably is conducted by connecting the electrode 33 to the lead 34 via the conductive adhesive 35, followed by baking in an oxygen-free atmosphere. Examples of the oxygen-free atmosphere include an atmosphere composed of at least one gas selected from nitrogen gas, argon gas, helium gas, and hydrogen gas.

Although a general metal paste can be used for the conductive adhesive 35, the conductive adhesive B described in Embodiment 2 preferably is used. More specifically, it is preferable to use a conductive adhesive containing Pt and Au or a conductive adhesive containing Al and Au.

According to the production method of Embodiment 3, by using a paste containing Au particles and Al particles, an electrode containing Au and Al easily can be formed. Therefore, according to the production method of Embodiment 3, a hydrocarbon sensor provided with electrodes having a high ability to block oxygen easily can be produced. Furthermore, according to the production method of Embodiment 3, by forming a metal paste in an oxygen-free atmosphere to form electrodes, a hydrocarbon sensor can be produced that contains a large amount of $AuAl_2$ and is provided with electrodes having a particularly high ability to block oxygen.

EXAMPLES

Hereinafter, the present invention will be described in more detail by way of illustrative examples. It should be noted that the present invention is not limited to the conditions in the following examples.

Example 1

In Example 1, exemplary production of the hydrocarbon sensor 10 of Embodiment 1 will be described.

First, an Au paste and an Al paste were mixed in various ratios. The mixture was printed over one surface of a substrate (corresponding to the substrate 11) made of a proton conductor and baked to form an electrode (corresponding to the cathode 12a). Baking was conducted in a nitrogen atmosphere at 850° C. At this time, a substrate made of $BaZr_{0.6}Ce_{0.2}Gd_{0.2}O_{3-\alpha}$ was used. TR1206 produced by Tanaka Kikinzoku Kogyo K. K. was used as the Au paste, and 9203C produced by Noritake Co., Ltd. was used as the Al paste. In Example 1, the weight ratio between the Au paste and the Al paste was varied to be 78:22, 75:25, . . . , 51:49, whereby 17 kinds of samples were produced.

Each electrode thus formed was subjected to quantitative analysis of its composition by X-ray diffraction. Furthermore, a Pt electrode was formed by baking onto the substrate as an anode to produce a hydrocarbon sensor. Each hydrocarbon sensor thus obtained was subjected to a heat cycle test in which an increase in temperature and a decrease in temperature were repeated 120 times from room temperature to 800° C. Then, I–V characteristics of the hydrocarbon sensor before and after the heat cycle were measured in an electric furnace capable of controlling an atmosphere, and a change in a current value at 1.0 volt caused by the heat cycle was measured. I–V characteristics of the hydrocarbon sensor before the heat cycle were measured in hydrogen and in the air (oxygen-containing atmosphere), and a ratio in a current value therebetween under the application of a voltage of 1.0 volt was calculated.

Table 1 shows an electrode composition obtained by the above-mentioned composition, an $AuAl_2/Au$ ratio in the electrode, a ratio between a current value in hydrogen and a current value in the air, and a change in a current value before and after the heat cycle.

TABLE 1

| No. | Electrode composition (mol %) $AuAl_2/Au/Al/Au_nAl_m$ | $AuAl_2/Au$ ratio | Current output ratio in hydrogen/in air | Change in current output before and after heat cycle |
|---|---|---|---|---|
| 1 | 34/21/—/45 | 62/38 | 2 to 3 | 5% to 20% |
| 2 | 43/21/—/36 | 67/33 | 3< | less than 5% |
| 3 | 78/22/—/— | 78/22 | 3< | less than 5% |
| 4 | 77/18/5/— | 81/19 | 3< | less than 5% |
| 5 | 72/23/5/— | 76/24 | 3< | 5% to 20% |
| 6 | 75/18/7/— | 81/19 | 3< | 5% to 20% |
| 7 | 72/21/7/— | 77/23 | 3< | 5% to 20% |
| 8 | 68/25/7/— | 73/27 | 3< | 5% to 20% |
| 9 | 70/21/9/— | 77/23 | 3< | 20%< |
| 10 | 62/27/11/— | 70/30 | 3< | 20%< |
| 11 | 63/24/13/— | 72/28 | 3< | 20%< |
| 12 | 76/10/14/— | 88/12 | 3< | 20%< |
| 13 | 63/20/17/— | 76/24 | 3< | 20%< |
| 14 | 45/28/7/20 | 62/38 | 2 to 3 | 5% to 20% |
| 15 | 32/26/10/32 | 55/45 | less than 2 | 20%< |
| 16 | —/28/—/72 | —/100 | less than 2 | 5% to 20% |
| 17 | 5/45/10/40 | 10/90 | less than 2 | 20%< |

In Table 1, $Au_nAl_m$ refers to an Au—Al alloy other than $AuAl_2$. A larger ratio of (current output in hydrogen)/(current output in the air) indicates a higher oxygen blocking ability of the electrode of the hydrocarbon sensor. Furthermore, a smaller change in a current output after the heat cycle indicates that a hydrocarbon sensor is more unlikely to be influenced by the heat cycle and has higher reliability.

As is apparent from Table 1, it was found that a hydrocarbon sensor containing 7 mol % or less of an initial Al simple substance (i.e., Al simple metal) in the electrode is unlikely to be influenced by the heat cycle and has higher reliability. An Al simple substance in the electrode gradually may be oxidized to become aluminum oxide ($Al_2O_3$) due to the heat cycle and the like during use. Therefore, considering such a state, by using an electrode satisfying a relationship: $a+2b \leq 7$ (assuming that a content of an Al simple substance in the electrode is "a" mol %, and a content of aluminum oxide in the electrode is "b" mol %), it is possible to obtain a highly reliable hydrocarbon sensor that is unlikely to be influenced by the heat cycle.

Furthermore, it was found from Table 1 that as a content of $AuAl_2$ in the electrode is higher, an oxygen blocking ability is more satisfactory. In particular, when an electrode contains $AuAl_2$ and an Au simple substance in a molar ratio of $AuAl_2:Au=X:1-X$ ($0.6 \leq X$), the oxygen blocking ability was very satisfactory.

In Example 1, the substrate made of $BaZr_{0.6}Ce_{0.2}Gd_{0.2}O_{3-\alpha}$ was used. However, even when a substrate made of $BaZr_{0.4}Ce_{0.4}In_{0.2}O_{3-\alpha}$ is used, the same results were obtained.

Example 2

In Example 2, exemplary production of the hydrocarbon sensor 20 in Embodiment 2 will be described.

First, a substrate (corresponding to the substrate 21) made of a proton conductor ($BaZr_{0.6}Ce_{0.2}Gd_{0.2}O_{3-\alpha}$ sintered body) having a size of 10 mm×10 mm and a thickness of 0.45 mm with an Au—Al type electrode (corresponding to the electrode 22) formed by baking thereon was prepared. As the Au—Al type electrode, an electrode having a composition of No. 2 and an electrode having a composition of No. 4 in Table 1 were used. Pt leads (corresponding to the leads 23a and 23b) with a diameter of 0.15 mm having high heat resistance and corrosion resistance were used. The leads and the electrodes were baked and attached to each other with various metal pastes (corresponding to the conductive adhesives 24a and 24b).

Each hydrocarbon sensor thus obtained was evaluated for an adhesion strength between the lead and the electrode by stretching the lead with a force of $4.9 \times 10^{-2}$ N (5 gf). Furthermore, a heat cycle test was conducted in which a cycle of room temperature to 800° C. was repeated 120 times. An adhesion strength between the lead and the electrode was checked by the same method. Table 2 shows the results.

TABLE 2

| No. | Metal paste Contained metal | Product No. | Immediately after baking | After heat cycle |
|---|---|---|---|---|
| 18 | Au | TR140 | B | — |
| 19 | | TR1206 | A | B |
| 20 | | N-2764 | A | B |
| 21 | | A-3360 | B | — |
| 22 | Pt | 1350A | B | — |
| 23 | | U3400 | A | A |
| 24 | | U3820 | A | A |
| 25 | | A-3444 | B | — |
| 26 | Ag | MH 2014 | B | — |
| 27 | Au/Al (60/40 mol %) | TR1206/9203C | A | A |
| 28 | Au/Al (57/43 mol %) | | A | A |
| 29 | Pt/Au (70/30 mol %) | U3400/TR1206 | A | A |
| 30 | Pt/Au (60/40 mol %) | | A | A |

In Table 2 and 4, "A" indicates the case where peeling and disconnection did not occur in the tensile test. "B" indicates the case where peeling and disconnection occurred in the tensile test. Furthermore, in Table 2, TR140, TR1206, and MH2014 indicate product nos. of metal pastes produced by Tanaka Kikinzoku Kogyo K. K. N-2764, A-3360, U3400, U3820, and A-3444 indicate product nos. of metal pastes produced by NE Chemcat Co., 9203C indicates a product no. of a metal paste produced by Noritake Co., Ltd.

were mixed in a ratio in the vicinity of a stoichiometric ratio of $AuAl_2$.

Thereafter, the baking conditions were changed, and the coating paste was baked, whereby an electrode was formed. The composition of the electrode thus obtained was analyzed. Table 3 shows the results.

TABLE 3

| No. | Conductive adhesive Au/Al ratio (wt %) | | Baking conditions | | Electrode composition (mol %) | |
|---|---|---|---|---|---|---|
| | Au | Al | Atmosphere | Baking temperature | $AuAl_2/Au/Al/Au_nAl_m$ | $AuAl_2Au$ ratio |
| 31 | | | Air | 850° C. | —/41/5/54 | —/100 |
| 32 | 78 | 22 | | 900° C. | —/32/2/66 | —/100 |
| 33 | | | Nitrogen | 850° C. | 10/24/3/63 | 29/71 |
| 34 | | | | 900° C. | 32/43/5/20 | 43/57 |
| 35 | 60 | 40 | Air | 850° C. | 52/26/9/13 | 67/33 |
| 36 | | | Nitrogen | | 63/20/17/— | 76/24 |
| 37 | 57 | 43 | Air | 850° C. | 58/21/9/12 | 73/27 |
| 38 | | | Nitrogen | | 72/23/5/— | 76/24 |
| 39 | 54 | 46 | Air | 850° C. | 68/18/9/5 | 79/21 |
| 40 | | | Nitrogen | | 75/18/7/— | 81/19 |
| 41 | | | Argon | | 73/22/5/— | 77/23 |
| 42 | 57 | 43 | Helium | 850° C. | 77/18/5/— | 82/18 |
| 43 | | | 3% $H_2$ | | 78/22/—/— | 78/22 |

As is apparent from Table 2, it was found that in the case where a metal paste contains Pt and Au, and in the case where a metal paste contains Au and Al, an adhesion strength between the Au—Al type electrode and the lead is high. Thus, according to Embodiment 2, a highly reliable hydrocarbon sensor is obtained without contact defects and disconnection.

The hydrocarbon sensor of the present invention is not limited to that of the present example regarding a solvent for a paste, a trace amount of a sub-component and a particle size of a binder and the like, and baking conditions. In Example 2, two kinds of mixtures of Au/Al and Pt/Au are described. Any mixing ratio thereof may be used. For example, a mixing ratio of 99 mol %/1 mol % (Pt/Au) may be used. Furthermore, any combination of commercially available pastes may be used. Needless to say, any structure and shape of an adhesive may be used. Furthermore, the composition and component of an electrode are not limited to those of the present example.

Example 3

In Example 3, exemplary production of a hydrocarbon sensor by the production method described in Embodiment 3 will be described.

First, a substrate (corresponding to the substrate 31) made of a proton conductor ($BaZr_{0.6}Ce_{0.2}Gd_{0.2}O_{3-\alpha}$ sintered body) was prepared, and the substrate was coated with a paste containing Au particles and Al particles to form a paste layer (corresponding to the layer 32). At this time, a mixing ratio between an Au paste (TR1206 produced by Tanaka Kikinzoku Kogyo K. K.) and an Al paste (9203C produced by Noritake Co., Ltd.) were varied, whereby pastes containing Au particles and Al particles were regulated. In order to form $AuAl_2$ in a large amount, an Au paste and an Al paste In Table 3, 3% $H_2$ of No. 43 refers to a nitrogen atmosphere containing 3 vol % hydrogen.

As is apparent from Table 3, by baking a paste containing Au particles and Al particles, an electrode composed of metal containing Au and Al was formed. Furthermore, by baking the paste in an oxygen-free atmosphere, a content of $AuAl_2$ in the electrode was enhanced. In particular, in the case where the above-mentioned Au paste (TR1206) and Al paste (9203C) were used, if the paste after mixing contained Au particles and Al particles in a weight ratio of Y:1–Y ($0.54 \leq Y \leq 0.6$), a content of $AuAl_2$ particularly was enhanced.

In the example shown in Table 3, an Au paste and an Al paste were mixed in a weight ratio of 78:22, 60:40, 57:43, and 54:46, and baked at 850° C. or 900° C. However, the present invention is not limited to the above-mentioned mixing ratio of a paste and baking conditions.

Next, regarding the production method described in Embodiment 3, exemplary production of a hydrocarbon sensor by changing, in particular, conditions of a lead connection process will be described.

First, under the condition of No. 36 or No. 38 in Table 3, an electrode (cathode) was formed on a substrate made of a proton conductor ($BaZr_{0.6}Ce_{0.2}Gd_{0.2}O_{3-\alpha}$ sintered body). Thereafter, a lead made of Pt and the electrode were connected to each other by using a conductive adhesive. At this time, a plurality of samples were produced by using different conductive adhesives and baking conditions. The samples thus obtained were subjected to a heat cycle test in which a cycle of room temperature to 800° C. was repeated 120 times. Each sample was evaluated for an adhesion strength between the lead and the electrode before and after the heat cycle by the same method as that in Example 2. Table 4 shows the evaluation results.

TABLE 4

| No. | Metal paste Contained metal | Product No. | Baking atmosphere | Immediately after baking | After heat cycle |
|---|---|---|---|---|---|
| 44 | Au/Al | TR1206/9203C | Air | A | A |
| 45 | (57/43 wt %) | | Nitrogen | A | A |
| 46 | Au/Al | TR1206/9203C | Air | A | B |
| 47 | (60/40 wt %) | | Nitrogen | A | A |
| 48 | Au/Al | TR1206/9203C | Air | B | — |
| 49 | (80/20 wt %) | | Nitrogen | A | A |
| 50 | Pt/Au | U3400/TR1206 | Air | A | A |
| 51 | (60/40 wt %) | | Nitrogen | A | A |
| 52 | Pt/Au | U3400/TR1206 | Air | A | B |
| 53 | (70/30 wt %) | | Nitrogen | A | A |
| 54 | Pt/Au | U3400/TR1206 | Air | B | — |
| 55 | (80/20 wt %) | | Nitrogen | A | A |
| 56 | | | Air | B | — |
| 57 | Pt/Au | | Nitrogen | A | A |
| 58 | (90/10 wt %) | U3400/TR1206 | Argon | A | A |
| 59 | | | Helium | A | A |
| 60 | | | 3% $H_2$ | A | A |

In Table 4, an electrode component is the same as a metal component contained in a conductive adhesive in No. 44 and in No. 45.

As is apparent from Table 4, by baking a conductive adhesive in an oxygen-free atmosphere, an initial adhesion strength and an adhesion strength after the heat cycle between the lead and the electrode was enhanced, whereby a highly reliable hydrocarbon sensor was produced.

In Example 3, the substrate made of $BaZr_{0.6}Ce_{0.2}Gd_{0.2}O_{3-\alpha}$ was used. However, even when a substrate made of $BaZr_{0.4}Ce_{0.42}In_{0.2}O_{3-\alpha}$ was used, the same results were obtained.

In the example shown in Table 4, a commercially available paste was baked at 850° C. in various atmospheres, whereby the lead was connected to the electrode. However, the present invention is not limited to the above-mentioned baking temperature and kind of a paste. For example, the baking temperature may be 900° C. Furthermore, in the example in Table 4, seven kinds of mixed pastes using different materials and mixing ratios were used. However, the present invention is not limited thereto. For example, a mixing ratio of 99 mol %/1 mol % (Pt/Au) may be used. Furthermore, any electrode other than that in the present example may be used as long as it is of an Au—Al type.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A hydrocarbon sensor comprising a substrate made of a solid electrolyte that conducts protons, a pair of electrodes formed on a substrate, and leads connected to the electrodes,
   wherein at least one electrode of the pair of electrodes contains Au and Al, and
   the at least one electrode and its lead are connected to each other via a conductive adhesive containing Pt and Au or a conductive adhesive containing Al and Au.

2. A hydrocarbon sensor according to claim 1, wherein the at least one electrode and its lead are connected to each other via a conductive containing Al and Au, and
   a component of the at least one electrode is the same as a component of metal contained in the conductive adhesive.

* * * * *

UNITED STATES PATENT AND TRADEMARK OFFICE
CERTIFICATE OF CORRECTION

PATENT NO.    : 6,638,406 B2
DATED         : October 28, 2003
INVENTOR(S)   : Taniguchi It is certified that error appears in the above-identified patent and that said Letters Patent is hereby corrected as shown below:

Column 12,
Line 34, "formed on a substrate" should read -- formed on the substrate --
Line 42, "a conductive containing A1" should read -- a conductive adhesive containing A1 --

Signed and Sealed this

Eighteenth Day of May, 2004

JON W. DUDAS
*Acting Director of the United States Patent and Trademark Office*